United States Patent [19]
Kloimstein et al.

[11] Patent Number: 5,939,580
[45] Date of Patent: Aug. 17, 1999

[54] PROCESS FOR PREPARING GLYOXYLIC ESTERS AND THEIR HYDRATES

[75] Inventors: Engelbert Kloimstein, Eferding; Wolfram Hendel, Leonding; Klaus Reiter, Linz; Christian Burger, Leonding; Antonia Praus, Linz; Karl Heinz Giselbrecht, Pasching; Eduard Perndorfer, Traun, all of Austria

[73] Assignee: DSM Fine Chemicals Austria GmbH, Austria

[21] Appl. No.: 08/976,089

[22] Filed: Nov. 21, 1997

[30] Foreign Application Priority Data

Nov. 21, 1996 [AT] Austria ..................................... 2032/96

[51] Int. Cl.⁶ ..................................................... C07C 69/66
[52] U.S. Cl. ............................ 560/186; 560/193; 560/194
[58] Field of Search ..................................... 560/177, 186, 560/877, 587, 193, 194

[56] References Cited

U.S. PATENT DOCUMENTS 3,145,232   8/1964   Thompson .
5,015,760   5/1991   Sajtos ...................................... 560/186

FOREIGN PATENT DOCUMENTS

WO96/22960   8/1996   WIPO .

OTHER PUBLICATIONS

CA 88: 49998 (1977).

*Primary Examiner*—Paul J. Killos
*Attorney, Agent, or Firm*—Wenderoth, Lind & Ponack, L.L.P.

[57] ABSTRACT

Process for preparing glyoxylic esters or their hydrates in which a water-soluble salt of a maleic or fumaric monoester or a mixture thereof is reacted with ozone in aqueous solution at temperatures of from 0 to 50° C., and the corresponding glyoxylic ester or its hydrate is isolated from the resulting reaction mixture.

7 Claims, No Drawings

PROCESS FOR PREPARING GLYOXYLIC ESTERS AND THEIR HYDRATES

Glyoxylic esters, such as ethyl glyoxylate, methyl glyoxylate and benzyl glyoxylate or L-(−)-menthyl glyoxylate, are important reagents in organic chemistry since the α-keto ester group is a very reactive group which can participate in a large number of reactions. L-(−)-Menthyl glyoxylate is, for example, an important $C_2$ building block for asymmetric syntheses, for chiral acetals, such as oxathiolanes, for stereocontrolled addition reactions to alkenes and nitroalkanes or for Grignard reactions.

The preparation of glyoxylic esters from corresponding maleic or fumaric diesters using a two-stage ozonolysis and reduction process is already known from several literature sources.

Thus, according to J. Org. Chem. 1982, 47, pp. 891–892, for example, ethyl, methyl or benzyl glyoxylates are obtained by ozonolysis of corresponding maleic diesters in dichloromethane, subsequent reduction of the ozonide using dimethyl sulfide and then distillation.

WO 96/22960 also describes a two-stage process for preparing menthyl glyoxylate as an intermediate for menthyl dihydroxyacetate, in which dimenthyl maleate or fumarate is ozonized in the first stage in a halogenated hydrocarbon or carboxylic ester, preferably in the presence of a lower aliphatic alcohol, and in the second stage the resulting ozonolysis product is reduced either with a dialkyl sulfide or by catalytic hydrogenation with hydrogen to give menthyl glyoxylate.

The disadvantage of the processes known to date is, however, that the ozonolysis step produces peroxide-containing ozonolysis products which then have to be reduced in a second step, either by catalytic hydrogenation or in the presence of dialkyl or aryl sulfides or trialkyl phosphides, to give the corresponding glyoxylic esters.

Unexpectedly, it has now been found that a water-soluble salt of a maleic or fumaric monoester or mixtures thereof can be ozonized in aqueous solution to give the corresponding glyoxylates, there being rapid decomposition of the peroxides which form, and the previously required reduction step being unnecessary.

Accordingly, the present invention provides a process for preparing glyoxylic esters or their hydrates, which comprises reacting a water-soluble salt of a maleic or fumaric monoester or a mixture thereof in aqueous solution at temperatures of from 0 to 50° C. with ozone, and isolating the corresponding glyoxylic ester or its hydrate from the resulting reaction mixture.

The starting compounds used in the process according to the invention are salts of maleic or fumaric monoesters or mixtures thereof. Suitable salts are those which lead to water-soluble compounds. Examples thereof are alkali metal salts or alkaline earth metal salts, such as sodium, potassium, calcium or magnesium salts. Preference is given to using the Na or K salts of the maleic or fumaric monoesters.

The ester moiety of the starting compounds used according to the invention can be derived either from chiral or from nonchiral alcohols. In the case of chiral alcohols, all available stereoisomers are suitable.

Preference is given to using esters of secondary or tertiary alcohols, in particular of acyclic, monocyclic, bicyclic terpene alcohols, of acyclic, monocyclic, tricyclic sesquiterpene alcohols, or di- or triterpene alcohols, all of which may be substituted.

Particular preference is given to esters which are derived from monocyclic or bicyclic terpene alcohols which may have different substituents, such as menthols, phenylmenthol, borneol, fenchol etc.

In the process according to the invention, preference is therefore given to using Na, K, Ca or Mg salts of maleic or fumaric monoesters, whose ester moiety is derived from chiral or nonchiral, secondary or tertiary alcohols. Examples thereof are the Na, K, Ca or Mg salts of monophenylmenthyl maleate, monomenthyl maleate, monofenchyl maleate, monobornyl maleate etc. and the analogous fumaric monoesters.

Some maleic and fumaric monoesters can be obtained commercially and can be converted directly as they are into the corresponding alkali metal salt or alkaline earth metal salt. It is, however, also possible to prepare the desired starting compounds firstly by reacting maleic anhydride (fumaric acid) with the corresponding alcohol, for example in the melt at temperatures of from 60 to 120° C. or in a suitable solvent which has a boiling point of approximately 80 to 120° C., preferably in toluene. The reaction can also be carried out in the presence of catalytic quantities of sulfuric acid or comparable acids. When reacting the two reactants, care should be taken to minimize diester formation.

The preparation of mono-L-menthyl maleate in the melt or in a suitable solvent is, for example, described in Annalen d. Chemie, 492, p. 273 (1935) or in Chem. Ber. 119, p. 3494 (1986). Other maleic and fumaric monoesters can, for example, be prepared analogously.

The monoesters can be extracted from the reaction mixture using bases, preferably using sodium hydrogen carbonate or sodium hydroxide or the corresponding base of other alkali metals or alkaline earth metals. The salts of maleic and fumaric monoesters having long aliphatic chains or alicyclic systems have excellent surfactant properties, meaning that some of the solvent used in the ester preparation is carried into the aqueous phase during extraction. However, since in some circumstances the presence of this solvent during the ozonolysis impedes the crystallization of the corresponding end products, if they are crystalline, it must be removed by azeotropic distillation prior to ozonolysis. In addition, some of these salts have a great tendency towards severe foaming when gas is introduced, making it advantageous to add an ozone-resistant antifoam to the ozonolysis solution. A silicone-based antifoam is preferably used. The amount of antifoam is approximately 0.01–0.2% by volume, preferably 0.05–0.15% by volume, based on the total amount of ozonolysis solution, and also depends on the extent of the tendency to foam.

The salt solutions may be subjected to a further extraction, preferably with toluene, prior to ozonolysis. The toluene mother liquors which are produced during monoester preparation and which contain small amounts of diester and alcohol can be returned to the esterification. Other suitable alkali metal or alkaline earth metal salts are obtained in a similar way. To carry out the ozonolysis, the salt solutions of maleic or fumaric monoesters or their mixtures obtained as described above may be further diluted with water.

The ozonolysis is carried out at temperatures of from 0 to 50° C., the temperature preferably being between 10 and 30° C. In the process according to the invention, an ozone-bearing $O_2$ stream is passed into the aqueous solution of the respective starting compound until the equivalent amount of ozone or a slight excess of ozone has been absorbed. The end and thus the duration of the reaction is given by the consumption of the theoretical amount of ozone and can also be readily established by an increased appearance of ozone which takes place simultaneously.

In the process according to the invention, the initially formed ozonide or hydroperoxide immediately decomposes into the corresponding end product and the corresponding cleavage product, for example into the corresponding glyoxylic ester hydrate and into sodium oxalate, the end product being free from peroxides.

Isolation of the corresponding glyoxylic ester or its hydrate takes place depending on the respective state of aggregation in which the end product is produced.

If, after ozonolysis is complete, the corresponding end product is in the form of a solid, then it is isolated, for example, by filtration from the obtained suspension. Subsequently, it is washed with water and the end product is dried under mild conditions, for example at temperatures of from 20 to 40° C. at a reduced pressure of <10 mbar. Depending on purity requirements, the end product can be further purified by recrystallization from hydrocarbons, for example from hexane, or from ethers, for example diisopropyl ether.

End products in the form of liquids can be isolated, for example, by extraction from the ozonolysis solution. Suitable extractants here are hydrocarbons, ethers or ethyl acetate. Following extraction, the organic phases are combined, washed with water and dried. Subsequently, the drying agent is filtered off, the solvent is preferably removed under reduced pressure and the remaining end product is dried.

The process according to the invention is thus suitable for the ozonization of water-soluble salts of maleic or fumaric monoesters or their mixtures. In particular, the process according to the invention is suitable for preparing glyoxylates and/or their hydrates of chiral and nonchiral alcohols, preferably secondary or tertiary alcohols and, particularly preferably, optionally differently substituted monocyclic and bicyclic terpene alcohols. The corresponding end products are obtained in good elds with high purity.

EXAMPLE 1 a) Preparation of mono-L-menthyl maleate 125.02 g (0.8 mol) of maleic anhydride and 117.67 g of L-menthol were refluxed in 400 ml of toluene for 4 hours with stirring.

(GC check, reaction is complete when the GC product peak constitutes approximately 90 to 94% area and is no longer increasing).

The reaction solution was then cooled to room temperature and washed twice, each time using 200 ml of water, to remove excess maleic anhydride. The two-phase mixtures were in each case allowed to stand for approximately 15 min to achieve complete separation.

The mono-L-menthyl maleate formed was then extracted into the aqueous phase using 1344 g of a 5% $NaHCO_3$ solution. Phase separation required approximately 1 hour. Small amounts of L-menthol and diester were removed with the organic phase and could be returned to the process.

Since mono-L-menthyl maleate, because of its surfactant properties, introduced considerable quantities of toluene into the aqueous phase, the latter were removed by azeotropic distillation.

Determination of sodium monomenthyl maleate content: NMR/HPLC approximately 1420–1460 g of a solution of the Na salt, content (HPLC): 12.5–14.0% contains approximately 180–200 g of sodium monomenthyl maleate (80–90%, theory: 221.04 g)

M.p.: 88.4° C.

$\alpha_D^{20}$=−76.8° (c=1, acetonitrile/water 95:5)

$^1$H-NMR ($CDCl_3$): δ=0.78 (d, J=7 Hz, 3H, $CH_3$), 0.88–0.95 (br m, 1H, menthyl H), 0.91 (d, 3H, CH($\underline{CH}_3$)$_2$), 0.94 (d, 3H, CH($\underline{CH}_3$)$_2$), 1.07–1.14 (br m, 2H, menthyl H), 1.44–1.53 (br m, 2H, menthyl H), 1.69–1.75 (br m, 2H, menthyl H), 1.75–1.86 (m, 1H, $\underline{CH}(CH_3)_2$), 2.04–2.08 (br m, 1H, menthyl-H), 4.86 (dt, J=4.4 Hz and 10.9 Hz, 1H, COO—CH), 6.35 (d, J=12.7 Hz, HC=C) 6.45 (d, J=12.7 Hz, HC=C) ppm b) Preparation of L-menthyl glyoxylate monohydrate 600 ml (611 g, 0.32 mol) of a sodium monomenthyl maleate solution prepared as described above were diluted with 400 ml of water and, with the addition of 1 ml of antifoam (Antifoam SRE, Wacker), an oxygen stream which contained 68 g of $O_3/m^3$ was passed in at 33–22° C. for 2 hours with stirring. 14.8 g of ozone were consumed (theory 14.4 g).

The white suspension resulting from ozonolysis was filtered, and the solid was slurried with 100 ml of water and sucked dry. The solid was washed twice more, each time using 100 ml of water, and dried at 30° C. under a reduced pressure of <10 mbar. 54.45 g (71%, based on L-(−)-menthol used and ozonized portion) of a white solid were obtained.

Purity: 97.1% (HPLC)

M.p.: 83–85° C. (from hexane)

$\alpha_D^{20}$=−74.5° (c=1, acetonitrile/water 95:5)

IR (KBr)=3423 and 3353 (OH), 2958, 2923, 2872, 2856, 1741 (C=O), 1460, 1376, 1312, 1290, 1224, 1100, 1035 $cm^{-1}$.

c) Preparation of the potassium salt 749 g (approximately 0.75 mol, content 27.8%) of a solution of sodium mono-L-menthyl maleate prepared as in 1a) were diluted with 400 ml of water and acidified to pH 1.6 using 153.1 g of 30% sulfuric acid. The lumpy precipitate was filtered off with suction, broken up and washed in 1 l of water and sucked dry. 246.2 g of moist carboxylic acid were taken up in 900 ml of water and dissolved by adding 155.4 g of 25% potassium hydroxide solution. The pH was adjusted to 7.5.

Determination of potassium monomenthyl maleate content NMR/HPLC, 1291 g of a solution of the K salt, content (HPLC): 15.8% contains approximately 204 g of potassium monomenthyl maleate (93%, theory 220.3 g)

d) Preparation of L-menthyl glyoxylate monohydrate 750 ml (0.48 mol) of a potassium monomenthyl maleate solution prepared as in 1c) were diluted with 250 ml of water and, with the addition of 1 ml of antifoam (Antifoam SRE, Wacker), an oxygen stream which contained 70 g of $O_3/m^3$ was passed in at 20° C. for 2.5 hours with stirring. 24.4 g of ozone were consumed (theory 23 g).

The white suspension resulting from ozonolysis was filtered, and the solid was slurried with 150 ml of water and sucked dry. The solid was washed twice more, each time using 150 ml of water, and dried at 30° C. under a reduced pressure of <10 mbar.

35.2 g (32%, based on the potassium salt used) of a white solid were obtained. Extraction of the mother liquor (in this case two-phase since the product had not completely crystallized) with toluene, after adjustment of the pH to 2, isolated a further 29.0 g of a colorless oil. This was a product highly contaminated with starting material, indicating that in this case ozonolysis was incomplete.

EXAMPLE 2 a) Preparation of mono-D-menthyl maleate 29.42 g (0.3 mol) of maleic anhydride and 31.25 g (0.2 mol) of D-(+)-menthol were refluxed in 100 ml of toluene for 4 hours with stirring. (GC check, reaction is complete when the GC product peak constituted 91% area).

The reaction solution was then cooled to room temperature and washed twice, each time using 50 ml of water, to remove excess maleic anhydride.

The two-phase mixtures were each left to stand in this case for approximately 15 min until complete separation had taken place.

The mono-D-menthyl maleate formed was then extracted into the aqueous phase using 336 g of a 5% $NaHCO_3$ solution. Phase separation took place spontaneously.

Toluene and menthol residues were removed by azeotropic distillation. 328 g=320 ml of Na salt solution.

M.p.: 84–86° C. (from hexane)

$\alpha_D^{20}$=+79.3° (c=1, acetonitrile/water 95:5)

$^1$H-NMR ($CDCl_3$): δ=0.78 (d, J=7 Hz, 3H, $CH_3$), 0.88–0.95 (br m, 1H, menthyl H), 0.91 (d, 3H, CH($\underline{CH}_3$)$_2$) 0.94 (d, 3H, CH($\underline{CH}_3$)$_2$), 1.07–1.14 (br m, 2H, menthyl H), 1.44–1.53 (br m, 2H, menthyl H), 1.69–1.75 (br m, 2H, menthyl H), 1.75–1.86 (m, 1H, $\underline{CH}(CH_3)_2$), 2.04–2.08 (br m, 1H, menthyl H), 4.86 (dt, J=4.4 Hz and 10.9 Hz, 1H, COO—CH), 6.35 (d, J=12.7 Hz, HC =C) 6.45 (d, J=12.7 Hz, HC=C) ppm b) Preparation of D-menthyl glyoxylate monohydrate 160 ml of the sodium monomenthyl maleate solution were diluted with 850 ml of water and, with the addition of 1 ml of antifoam (Antifoam SRE, Wacker), an oxygen stream which contained 29 g of $O_3/m^3$ was passed in at 20° C. for 2.25 hours with stirring. 5.4 g of ozone were consumed (theory 4.3 g). The white suspension resulting from ozonolysis was filtered, and the solid was washed three times, each time using 30 ml of water, and dried at 30° C. under a reduced pressure of <10 mbar.

15.3 g (65%, based on D-(+)-menthol used and ozonized proportion) of a white solid were obtained.

Purity: 97.9% area (GC), content: 95.7% w/w

M.p.: 78.8° C.

$\alpha_D^{20}$=+74.40° (c=1, acetonitrile/water 95:5)

IR (KBr)=3423 and 3353 (OH), 2959, 2923, 2872, 2856, 1742 (C=O), 1460, 1377, 1234, 1223, 1100, 1035 $cm^{-1}$.

EXAMPLE 3 a) Preparation of monobornyl maleate 7.35 g (0.075 mol) of maleic anhydride and 7.71 g (0.05 mol) of 1S-endo-(-)-borneol were refluxed in 20 ml of toluene for 3 hours with stirring. (GC check, reaction 93.7% area, 2.9% area borneol). The reaction solution was then cooled to room temperature and washed twice, each time using 50 ml of water, to remove excess maleic anhydride.

The monobornyl maleate formed was then extracted into the aqueous phase using 79.8 g of a 5% $NaHCO_3$ solution over the course of 30 min. Phase separation produced a copious white precipitate which was redissolved by the addition of a further 300 ml of water. The aqueous phase was again removed and residual toluene was removed by azeotropic distillation.

341.7 g of an aqueous solution of sodium monobornyl maleate were obtained.

141.23 g of an aqueous solution of sodium monobornyl maleate were adjusted to pH 1 using 30 ml of 1M HCl and extracted twice with 100 ml of toluene. The toluene phases were combined and dried over $Na_2SO_4$. Filtering off the drying agent and stripping off the solvent under reduced pressure produced 4.8 g (76%) of a colorless oil which solidified to crystals when left to stand overnight at 5° C. (m.p. 44–48° C.). Recrystallization of 4.5 g of the compound from 15 ml of n-hexane produced 3.32 g.

Purity 98.4% area GC.

m.p.: 52.3° C.

$\alpha_D^{20}$=−45.1° (c=acetonitrile/water 95:5)

$^1$H-NMR (DMSO): δ=0.83 (s, 3H, $CH_3$), 0.87 (s, 3H, $CH_3$), 0.90 (s, 3H, $CH_3$), 1.07 (dd, 1H, 3 endo-H), 1.18–1.31 (m, 2H, 5 endo-H, 6 endo-H), 1.68–1.78 (m, 2H, 4,5 exo-H), 1.85–1.94 (m, 1H, 6 exo-H), 2.23–2.33 (m, 1H, 3 exo-H), 4.87 (m, 1H, 2 exo-H), 6.33 (d, J 12.1 Hz, 1H, CH=C), 6.39 (d, J=12.1 Hz, 1H, CH=C) ppm b) Preparation of bornyl glyoxylate monohydrate 311.2 g of the above sodium salt solution were ozonized for 25 min at room temperature (ozone consumption approximately 7.4 g), with the addition of approximately 2 g of an antifoam (Antifoam SRE, Wacker). The solution became viscous after approximately 10 min. The ozonolysis solution was washed out of the apparatus and extracted using 200 ml of toluene. Extraction was then carried out using another 50 ml of toluene. The combined toluene phases were washed with 100 ml of water and dried over $Na_2SO_4$. After filtering off the drying agent, the solvent was removed under reduced pressure and the remaining oily residue was dried at <1 mbar.

5.8 g (61%) of an oily compound were obtained.

Purity (GC): 96.2% area.

IR (KBr): 3450 (OH), 2954, 2881, 1744 (C=O), 1455, 1390, 1221, 1114, 885, 822

$^1$H-NMR ($CDCl_3$): δ=0.75, 0.79, 0.81, 0.82, 0.84, 0.85, 0.87 (7s, 9H, 1-$CH_3$ and C($CH_3$)$_2$), 0.97–1.05 (m, 1H, 3 endo-H), 1.15–1.30 (m, 2H, 5 endo, 6 endo-H), 1.64–1.73 (m, 2H, 4,5 exo-H), 1.83–1.90 (m, 1H, 6 exo-H), 2.28–2.37 (m, 1H, 3 exo-H), 3.90–4.20 (very broad <2H, CH(OH)$_2$), 4.86–5.03 (m, 1H, 2 exo-H), 5.19–5.29 (3s, <1H, —CH(OH)$_2$), 9.35 (s, about 0.2H, —CH=O)

EXAMPLE 4 a) Preparation of monofenchyl maleate 29.42 g (0.3 mol) of maleic anhydride and 30.85 g (0.2 mol) of (1R)-endo-(+)-fenchyl alcohol were refluxed in 100 ml of toluene for 8 hours with stirring. (GC check, reaction 85% area, 6% fenchyl alcohol).

The reaction solution was then cooled to room temperature and washed twice, each time using 70 ml of water, to remove excess maleic anhydride. The monofenchyl maleate formed was then extracted into the aqueous phase using 336 g of a 5% $NaHCO$, solution over the course of 20 min and left to stand for 15 min for phase separation to take place. The aqueous phase was removed and residual toluene was removed by azeotropic distillation. 364.2 g of an aqueous solution of sodium monofenchyl maleate were obtained.

91 g of this solution were adjusted to pH 1.5 using 12 ml of 30% $H_2SO_4$ and extracted using 120 ml of toluene. The toluene phase was washed with 60 ml of water and dried over $Na_2SO_4$. Filtering off the drying agent, stripping off the solvent under reduced pressure and drying at <1 mbar produced 11.15 g (88%) of a clear, yellowish, oily liquid. The substance crystallized in a deep-freeze compartment, but melted at room temperature. The m.p. was therefore between 0 and 5° C.

$\alpha_D^{20}$=+34.3° (c=1, acetonitrile/water 95:5)

$^1$H-NMR (DMSO): δ=0.75 (s, 3H, $CH_3$), 1.05 (s, 3H, $CH_3$), 1.08 (s, 3H, $CH_3$), 1.00–1.12 (m, 1H, fenchyl H), 1.19 (d, 1H, fenchyl H), 1.38–1.49 (m, 1H, fenchyl H), 1.60–1.77 (m, 4H, fenchyl H), 4.36 (s, 1H, COO—CH), 6.28 (d, 1H, J=12.1 Hz, HC=C), 6.46 (d, 1H, J=12.1 Hz, HC=C) ppm b) Preparation of fenchyl glyoxylate monohydrate 222 g of the above sodium salt solution were diluted with 128 g of water and, with the addition of approximately 2 g of antifoam (Antifoam SRE, Wacker), were ozonized for 2 hours at room temperature (ozone consumption approximately 6.6 g). The solution became viscous after approximately 20 min.

The ozonolysis solution was washed out of the apparatus and extracted using 300 ml of toluene. The toluene phase was washed with 100 ml of water and dried over $Na_2SO_4$.

After the drying agent had been filtered off, the solvent was removed under reduced pressure and the remaining oily residue was dried at <1 mbar. 1.4 g (48%) of a yellowish, slightly cloudy oil were obtained.

Purity GC: 97.1% area.

The product was obtained as crystals from a mixture of 15 ml of diethyl ether and 100 ml of n-hexane. The yield was 5.85 g. Evaporating the mother liquor produced two further crystal fractions, making the total yield of crystalline material 8.59 g.

M.p.: 98° C.

$\alpha_D^{20}$=+32.70° (c=1, acetonitrile/water 95:5)

IR (KBr): 3459 (OH) 2958, 2856, 1734 (C=O), 1463, 1390, 1386, 1237, 1228, 1118, 1023, 992, 977, 632 cm$^{-1}$.

EXAMPLE 5 a) Preparation of mono-8-phenylmenthyl maleate 0.59 g (6 mmol) of maleic anhydride and 0.93 g (4 mmol) of (−)-8-phenylmenthol were refluxed in 6 ml of toluene for 46 hours with stirring. (GC check, reaction 86% area, 12% 8-phenylmenthol). The reaction solution was then cooled to room temperature and washed twice, each time using 3 ml of water, to remove excess maleic anhydride.

The mono-8-phenylmenthyl maleate formed was then extracted into the aqueous phase using 6.7 g of a 5% NaHCO$_3$ solution over the course of 15 minutes and this phase was diluted with 14 ml of water. The resulting white emulsion was left to stand overnight for phase separation to take place. The aqueous phase was separated off and the residual toluene was removed by azeotropic distillation. 17.65 g of an aqueous solution of sodium mono-8-phenylmenthyl maleate were obtained.

3.5 g of this solution were adjusted to pH 1.5 using 0.3 ml of 30% H$_2$SO$_4$ and extracted using 2 ml of toluene. The toluene phase was washed with 5 ml of water and dried over Na$_2$SO$_4$. Filtering off the drying agent, stripping off the solvent under reduced pressure and drying at <1 mbar gave 0.19 g (68%) of a clear, colorless oil.

$^1$H-NMR (DMSO): δ=0.85 (d, J=6.4 Hz, 3H, phenylmenthyl CH$_3$), 0.80–1.15 (br m, 4H, phenylmenthyl H), 1.20 (s, 3H, C(C$_6$H$_5$)CH$_3$)$_2$), 1.27 (s, 3H, C(C$_6$H$_5$) (CH$_3$)$_2$) 1.35–1.60 (br m, 4H, phenylmenthyl H), 1.89 (br d, 1H, phenylmenthyl H), 1.96–2.05 (br dt, 1H, phenylmenthyl H), 4.76 (dt, J=4.2 Hz, J=10.7 Hz, 1H, COO—CH), 5.69 (d, 1H, J=12.0 Hz, HC=C), 6.21 (d, 1H, J=12.0 Hz, HC=C), 7.1–7.3 (m, 5H, Ar H) ppm b) Preparation of 8-phenylmenthyl glyoxylate 14.1 g of the above sodium salt solution were ozonized for 8 min with the addition of 2 drops of antifoam (Antifoam SRE, Wacker). The solution became viscous after approximately 3 minutes. The ozonolysis solution was flushed out of the apparatus and extracted using 20 ml of toluene.

Extraction was then carried out with a further 10 ml of toluene. The combined toluene phases were washed twice, each time using 10 ml of water, and dried over Na$_2$SO$_4$. After filtering off the drying agent, the solvent was removed under reduced pressure and the remaining oily residue was dried at <1 mbar. 0.39 g (42%) of a pink oil were obtained.

Purity GC: 96.7% area.

$^1$H-NMR spectra were recorded using a Bruker 300 MHz instrument.

We claim:

1. A process for preparing glyoxylic esters or their hydrates, which comprises reacting a water-soluble salt of a maleic or fumaric monoester or a mixture thereof in aqueous solution at temperatures of from 0 to 50° C. with ozone, and isolating the corresponding glyoxylic ester or its hydrate from the resulting reaction mixture.

2. The process as claimed in claim 1, wherein the salt used is a sodium, potassium, calcium or magnesium salt of a maleic or fumaric monoester or a mixture thereof.

3. The process as claimed in claim 1, wherein the maleic or fumaric monoesters used are esters of chiral or nonchiral alcohols.

4. The process as claimed in claim 3, wherein the maleic or fumaric monoesters used are esters of secondary or tertiary alcohols.

5. The process as claimed in claim 3, wherein the maleic or fumaric monoesters used are esters of optionally differently substituted acyclic, monocyclic, bicyclic terpene, sesquiterpene, di- or triterpene alcohols.

6. The process as claimed in claim 1, wherein an ozone-resistant antifoam is added to the ozonolysis solution.

7. The process as claimed in claim 1, wherein the glyoxylic ester or its hydrate is isolated from the reaction mixture by filtration or extraction and subsequent drying in each case, depending on the state of aggregation in which the ester is produced.

* * * * *